US009486651B2

United States Patent
Karczmar et al.

(10) Patent No.: US 9,486,651 B2
(45) Date of Patent: Nov. 8, 2016

(54) MRI-GUIDED HIFU MARKING TO GUIDE RADIOTHERAPY AND OTHER PROCEDURES

(75) Inventors: Gregory Karczmar, Crete, IL (US); Shunmugavelu Sokka, Brighton, NY (US); Charles A. Pelizzari, Western Springs, IL (US)

(73) Assignees: KONINKLIJKE PHILIPS N.V., Eindhoven (NL); THE UNIVERSITY OF CHICAGO, Chicago, IL (US)

( * ) Notice: Subject to any disclaimer, the term of this patent is extended or adjusted under 35 U.S.C. 154(b) by 2059 days.

(21) Appl. No.: 12/531,495

(22) PCT Filed: Mar. 7, 2008

(86) PCT No.: PCT/IB2008/050843
§ 371 (c)(1),
(2), (4) Date: Sep. 16, 2009

(87) PCT Pub. No.: WO2008/120117
PCT Pub. Date: Oct. 9, 2008

(65) Prior Publication Data
US 2010/0106005 A1    Apr. 29, 2010

Related U.S. Application Data

(60) Provisional application No. 60/909,061, filed on Mar. 30, 2007.

(51) Int. Cl.
*A61N 7/00*    (2006.01)
*A61B 5/00*    (2006.01)
(Continued)

(52) U.S. Cl.
CPC ............... *A61N 7/02* (2013.01); *A61N 5/1049* (2013.01); *A61B 90/39* (2016.02); *A61B 2090/374* (2016.02); *A61B 2090/376* (2016.02); *A61N 2005/1061* (2013.01)

(58) Field of Classification Search
CPC combination set(s) only.
See application file for complete search history.

(56) References Cited

U.S. PATENT DOCUMENTS 6,716,184 B2 *    4/2004    Vaezy et al. ............... 601/3
6,718,055 B1 *    4/2004    Suri ...................... 382/128
(Continued)

FOREIGN PATENT DOCUMENTS

WO        0182777 A2    11/2001
WO    2004075987 A1     9/2004
(Continued)

OTHER PUBLICATIONS

Silverman, R. H., et al.; Improved Visualization of High-Intensity Focused Ultrasound Lesions; 2006; Ultrasound Med Biol.; 32(11)1743-1751.

*Primary Examiner* — Katherine Fernandez
*Assistant Examiner* — Farshad Negarestan

(57) ABSTRACT

The present disclosure provides for effective systems and methods for increasing target tissue conspicuity within a particular anatomy of a particular patient. In an exemplary embodiment, a system associated with the present disclosure includes: (a) a MRI-guided HIFU system for generating ablation markings on a target tissue region, the MRI-guided HIFU system including a transducer for delivering HIFU to the target tissue region, the delivered HIFU generating the ablation markings on the target tissue and an MRI imaging system adapted to generate a three dimensional image of the target tissue region during HIFU delivery for guiding the delivery of the HIFU to the target tissue region; (b) a radiotherapy delivery system for delivering radiotherapy treatment to the target tissue region; and (c) a CT imaging system operable within the radiotherapy delivery system for generating a three dimensional image of the target tissue region. The markings generated on the target tissue region by the MRI-guided HIFU are visible in the image generated by the CT imaging system. The image generated by the CT imaging system guides the location of the radiotherapy treatment delivered to the target tissue region.

22 Claims, 1 Drawing Sheet

(51) Int. Cl.
  *A61B 5/055* (2006.01)
  *A61N 7/02* (2006.01)
  *A61N 5/10* (2006.01)

(56) References Cited

U.S. PATENT DOCUMENTS

2005/0084538 A1* 4/2005 Dayton et al. ............... 424/489
2006/0004281 A1* 1/2006 Saracen ....................... 600/414
2006/0058648 A1* 3/2006 Meier et al. .................. 600/436
2006/0293598 A1* 12/2006 Fraser .......................... 600/439
2007/0195929 A1* 8/2007 Ruchala et al. ................ 378/65
2008/0033420 A1* 2/2008 Nields et al. ................... 606/27

FOREIGN PATENT DOCUMENTS

| WO | 2005030330 A1 | 4/2005 |
| WO | 2006005021 A2 | 1/2006 |

\* cited by examiner

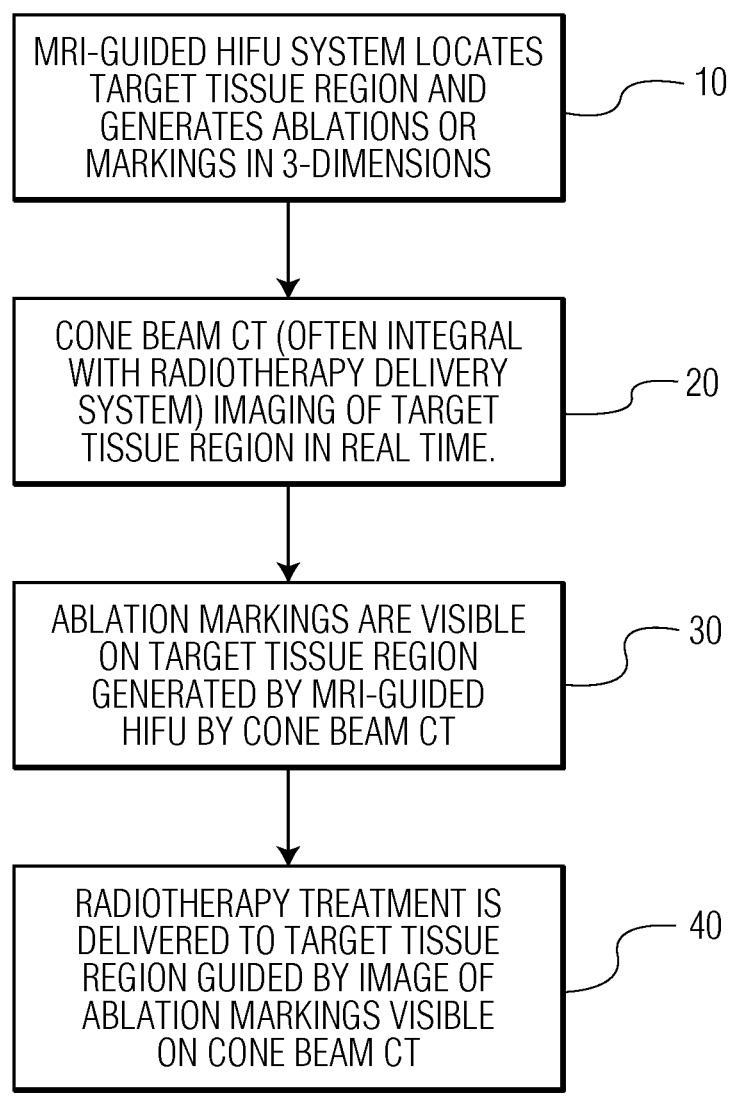

MRI-GUIDED HIFU MARKING TO GUIDE RADIOTHERAPY AND OTHER PROCEDURES

CROSS REFERENCE TO RELATED APPLICATIONS

This application claims the benefit of U.S. provisional application Ser. No. 60/909,061 filed Mar. 30, 2007, which is incorporated herein by reference.

The present disclosure relates to systems and methods for enhancing the conspicuity of target tissue regions to allow for improved image guidance associated with radiotherapy treatment and surgery.

Therapeutic ultrasound is a minimally invasive or non-invasive method to deposit acoustic energy into tissue. Applications of ultrasound therapy include tissue ablation (for tumor treatments, for example), hyperthermia treatments (low-level heating combined with radiation or chemotherapy), or the activation or enhanced delivery of drugs. High intensity focused ultrasound (HIFU; sometimes referred to as FUS or HIFUS) is a highly precise medical procedure using high-intensity focused ultrasound to heat and destroy pathogenic tissue rapidly. HIFU is one particular modality of therapeutic ultrasound. Typically under computerized MRI guidance, this technique can be referred to as Magnetic Resonance guided Focused Ultrasound, often shortened to MRgFUS or MRI-guided HIFU. Magnetic resonance imaging (MRI) is used to identify tumors or fibroids, associated with a particular anatomy, before they are destroyed by the ultrasound therapy.

Tracking tumor location and activity during radiotherapy is a difficult task, but is critical to directing proper radiotherapy beam placement. Correct beam placement directed to a target location becomes increasingly important as the capacity to control the deposition of dose by X-ray beams or particle beams (i.e. proton beams) improves. Improvements in radiation beam precision is expected to lead to improved therapeutic outcome. For example, using a more precise beam allows for maximizing radiotherapy dosage to a desired target location such as a tumor, while minimizing irradiation of nearby normal tissues. Conversely, increased beam precision and intensity increases the potential to harm surrounding tissue or normal tissue if there are errors in beam placement. Improving beam precision and intensity creates very steep gradients in the energy deposition resulting from radiation beams. This effect is especially profound when using proton beams.

Cone beam CT, whether performed with a megavoltage X-ray therapy beam or a diagnostic quality X-ray imaging system integrated with the therapy machine, is particularly helpful in monitoring beam placement because it allows imaging of a patient and/or target location immediately prior to receiving therapy. Kilovoltage or megavoltage radiography also allow acquisition of spatial information during therapy in the form of 2-dimensional projections. Although certain technologies allow for radiation therapy beams to be very precisely guided with respect to a defined target location such as a tumor, the effectiveness may be greatly reduced when the location of the tumor cannot be accurately tracked in the therapy machine. This is an important practical issue because portal beam imaging units mounted in therapy machines provide very poor soft tissue contrast. Moreover, CT in general and especially 'on board' cone beam CT, even with kilivoltage X-rays, have relatively poor soft tissue contrast. Thus, it is usually not possible to see a tumor within a particular patient or target location. Moreover, it is especially difficult to see and/or track the motion of a tumor due to respiration and other types of patient motion. As a result it is often necessary to use surrogate markers to demonstrate the location of a tumor and its potential movement. For example, CT detectable markers can be placed on the skin of a patient and the relationship between these markers and a particular tumor position is measured so that these markers can be used as a surrogate for the position of the tumor. This is far from ideal because the relationship between tumor and markers can change depending on a patient's relative position and motion including internal motion of the tumor relative to surrounding tissue and organs. Implanted markers can also be used but marker implantation is typically complicated, invasive and the relationship between markers and tumors may still change over time.

Lack of information related to tumor position and tumor motion during radiotherapy is a major impediment to optimal use of several therapy techniques/systems such as Intensity-Modulated Radiation Therapy (IMRT) and particle beam therapy systems. Accordingly, a need exists for an effective radiotherapy delivery system capable of effectively monitoring tumor location while simultaneously improving radiotherapy delivery. These and other needs are addressed and/or overcome by the systems and methods of the present disclosure.

The present disclosure provides for effective systems and methods for increasing target tissue conspicuity within a particular anatomy of a particular patient. In an exemplary embodiment, a system associated with the present disclosure includes: (a) a MRI-guided HIFU system for generating ablation markings on a target tissue region, the MRI-guided HIFU system including a transducer for delivering HIFU to the target tissue region, the delivered HIFU generating the ablation markings on the target tissue and an MRI imaging system adapted to generate a three dimensional image of the target tissue region during HIFU delivery for guiding the delivery of the HIFU to the target tissue region; (b) a radiotherapy delivery system for delivering radiotherapy treatment to the target tissue region; and (c) an X-ray, CT or radiographic imaging system operable within the radiotherapy delivery system for generating a three dimensional image of the target tissue region. The markings generated on the target tissue region by the MRI-guided HIFU are visible in the image generated by the X-ray imaging system. The image generated by the X-ray imaging system guides the location of the radiotherapy treatment delivered to the target tissue region.

The target tissue region can be any region intended to receive radiotherapy treatment and is often a tumor. In an exemplary embodiment, ablation markings form a three dimensional pattern on the target tissue region such that the pattern is effectively visible by the X-ray imaging system. The pattern of ablation markings can be a series of dots strategically positioned to provide boundaries for radiotherapy treatment delivery.

In an exemplary embodiment, the ablation markings are strategically generated on the target tissue region such that a contrast agent can be delivered intravenously (IV) to the target tissue region. The HIFU can be used to fix the contrast agent in the tissue at a point where the contrast agent concentration is maximized following IV injection. Two exemplary techniques include but are not limited to: 1) HIFU is used to coagulate blood vessels in a certain region thus trapping the contrast agent at the point where concentration is at a maximum. Although somewhat similar to chemo-embolization methods used to treat liver cancer, using HIFU allows for ablation of blood vessels in a small well defined area so that the trapped contrast agent makes a very clear mark; and 2) Apply HIFU at a low power just before injection of contrast agent to increase vascular permeability but not ablate the blood vessels. This can increase the leakage of contrast agent into the selected region. In an exemplary embodiment, these techniques are used in combination. The contrast agent can be any member selected from the group consisting of iron oxides, gadolinium X-ray agents, conventional iodinated X-ray agents, and combinations thereof. In an exemplary embodiment, the contrast agent delivered to the target tissue region is visible by other imaging systems including X-ray, MRI, and ultrasound.

In an exemplary embodiment, the MRI-guided HIFU system, the X-ray imaging system, and the radiotherapy delivery system are being used simultaneously and the X-ray imaging system is utilized at the radiotherapy machine. The radiotherapy treatment delivered to the target tissue region can be any radiotherapy treatment adapted to eliminate undesired tissue within the target tissue region. The radiotherapy treatment can be a member selected from the group consisting of chemotherapy and IMRT In an exemplary embodiment, the MRI-guided HIFU system is adapted to delineate target tissue regions more clearly when viewed by the CT imaging system. Radiotherapy treatment delivered to the target tissue region can be a radiotherapy beam and the positioning of the radiotherapy beam is continuously adjusted in real time thereby increasing dosage directed to the target tissue region and simultaneously reducing radiation exposure to surrounding non-target tissue regions.

In an exemplary embodiment, the ablation markings are generated non-invasively and sustain their visibility under tissue deformation. The ablation markings can be encoded and adapted to be registered and verified in future imaging of the target tissue region for future treatment planning strategy. In an exemplary embodiment, the MRI-guided HIFU system is utilized to provide image guidance to a surgeon performing surgery on the target tissue region. In a further exemplary embodiment, the contrast agent is gold beads adapted to enhance radiation effects. Exemplary ablation markings associated with the present disclosure can also provide for biopsy guidance.

The present disclosure provides for an effective method of increasing the conspicuity of a target tissue region for receiving radiotherapy including the steps of: (a) generating ablation markings on the target tissue region by ablating the target tissue region and/or also using the ablation to trap MRI detectable or optically detectable contrast agents with a MRI-guided HIFU system including a transducer adapted to deliver HIFU to target locations on the target tissue region guided by an MRI imaging system; (b) monitoring the position and/or location of the target tissue region using a CT imaging system operable within a radiotherapy delivery system; and (c) delivering radiotherapy treatment to the target tissue region by the radiotherapy delivery system. The markings generated on the target tissue region by the MRI-guided HIFU are visible by the CT imaging system and the CT imaging system is adapted to provide guidance to the delivery of the radiotherapy treatment by the radiotherapy delivery system. In an exemplary embodiment, the target tissue region is a tumor.

Additional features, functions and benefits of the disclosed systems and methods will be apparent from the description which follows, particularly when read in conjunction with the appended FIGURES.

To assist those of ordinary skill in the art in making and using the disclosed systems and methods, reference is made to the appended FIGURES, wherein:

FIG. 1 is a schematic flow chart for exemplary systems and methods associated with the present disclosure.

The present disclosure provides for systems and methods that utilize MRI-guided HIFU to delineate tumor margins more clearly. In an exemplary embodiment, MRI-guided HIFU can effectively delineate tumor margins in simultaneous use with portal CT imaging of tumors within a particular patient and/or anatomy associated with the patient. Although reference is made to cone beam CT, exemplary embodiments associated with the present disclosure include utilizing MRI-guided HIFU in combination with other imaging modalities and systems during therapy of a tumor.

In an exemplary embodiment, MRI-guided HIFU (or other MRI-guided thermal ablation techniques) allows for direct visualization of a particular tumor and surrounding tissue by cone beam CT, and thus greatly improves monitoring of the tumor location and tumor motion during a particular exemplary therapy treatment. Therapy treatments associated with the present disclosure include but are not limited to any exemplary radiotherapy treatment effective in treatment and reduction of tumor growth within a particular anatomy. MRI-guided HIFU allows for the use of marking target tissue regions non-invasively with an accuracy of 1-2 mm using CT contrast changes on the order of 5 mm in size. In addition, HIFU generated markings can be used to register planning and follow-up images from other imaging modalities such as MRI and/or ultrasound to improve radiation site selection and treatment follow-up.

The present disclosure provides for systems and methods directed to enhancing the conspicuity of target tissue regions such as tumors dramatically by marking a pattern detailing a 3-dimensional structure of the tumor using MRI-guided HIFU. Typically, when using a CT scan imaging modality or system, tissue ablated at high temperature or insonified with mechanical forces is much more conspicuous than untreated tissue. If further increases in conspicuity are needed, contrast agents can be precisely fixed and/or immobilized into lesions using MRI-guided HIFU. Exemplary contrast agents include but are not limited to iron oxides, Gadolinium, gold particles or conventional iodinated X-ray contrast agents.

In an exemplary embodiment, using MRI-guided HIFU marking allows for real time measurement and/or monitoring of tumor activity such as location and motion during a particular tumor related treatment such as radiotherapy treatment. Moreover, in an exemplary embodiment, MRI-guided HIFU marking allows for tumor monitoring such that continuous adjustments of a particular therapy beam associated with a particular radiotherapy treatment can be made during radiation delivery, thus improving therapy efficiency and precision. By adjusting exemplary therapy beams to account for motion during treatment of a tumor, for example, radiation dosage to the particular target tissue region and/or surrounding tissue can be increased while simultaneously decreasing radiotherapy exposure to normal tissue. An exemplary system associated with the present disclosure includes a tumor marking and monitoring system and/or method that is non-invasive and will maintain its tagging under tissue deformation which is often expected over a series of therapy treatments in slight varying positions.

In an exemplary embodiment according to the present disclosure, HIFU tagged tumor locations are visible and trackable during ultrasound and MRI imaging. If ultrasound and/or MRI imaging is used for radiation therapy planning and follow-up treatment, then the tagging of the tumors using MRI-guided HIFU is effective for registration and verification of successful treatment. In an exemplary embodiment, markings made by HIFU treatment are encoded for future use since many patients receiving radiotherapy may also receive HIFU treatment as an adjunct to radiation and chemotherapy.

The present disclosure relates to systems and methods effective for improving targeting of tumors during radiation therapy treatment using cone beam CT imaging. With MRI imaging playing an increased role in radiation oncology planning, HIFU markers can be used to register plans from the MRI imaging with the cone beam CT imaging. In an exemplary embodiment associated with the present disclosure, HIFU marking(s) are placed directly on a particular target tissue region such as a tumor and/or surrounding tissue. An HIFU transducer, adapted to deliver HIFU to the target tissue region, generates markings on the target tissue region. Effective control over the pattern of the marks in 3-dimensions is possible when guided through MRI imaging. The marks can be encoded under MRI-guidance so that the soft-tissue contrast resulting from an MRI image can be used to accurately determine tumor boundaries and 'high risk' areas within tumors where boost doses of radiation may be helpful. In an exemplary embodiment, markings on the tumor are generated using MRI-guided thermal ablation technologies.

Referring to FIG. 1, an exemplary schematic flow chart illustrates steps associated with an effective system/method according to the present disclosure. Box 10 represents the locating and ablation marking of a target tissue region using an MRI-guided HIFU system. Box 20 represents imaging of the target tissue region by an exemplary imaging system such as a cone beam CT. In an exemplary embodiment, the cone beam CT imaging system is integral with the radiotherapy delivery system. Box 30 represents monitoring by the cone beam CT of the position and location of the target tissue region ablated by the MRI-guided HIFU system. Box 40 represents a radiotherapy delivery system adapted to deliver radiotherapy treatment to the target tissue region. The imaging of the ablated target tissue region provides effective guidance with respect to the precision and intensity of the radiotherapy treatment.

In an exemplary embodiment, target tissue regions such as tumors, ablated by HIFU show up on an image with significantly enhanced contrast over a non-ablated image of the tumor when the image is created by an exemplary imaging system such as a CT, MR and/or ultrasound imaging system. In an exemplary embodiment, the target tumor and/or tissue is ablated generating precise lesions and/or lesion margins under MRI-guidance using HIFU. In a further exemplary embodiment, the location of the lesion(s) is trackable during treatment using 2-dimensional radiography or cone beam CT.

The present disclosure provides for an exemplary method for inducing trackable markers with respect to a target tissue region such as a tumor. In a particular exemplary method, high temperature ablation is used to create a maximum contrast for a CT imaging system. In a further exemplary method, short high intensity pulses are used to induce cavitations or a mechanical disruption at a HIFU focus with respect to a tumor and/or tumor margins. These high intensity pulses generate a series of little 'dots' around the surface of a lesion resulting from the HIFU. The dots are primarily generated to delineate lesion margins in 3-dimensional imaging. In an exemplary embodiment, the total volume insonified is relatively small to facilitate rapid execution of the ablation/marking procedure. In a further exemplary embodiment, HIFU ablation provides the additional benefit of further tumor ablation when used in combination with a particular radiation treatment such as IMRT to further ablate the tumor in combination with providing tumor position and location monitoring for the IMRT.

In an exemplary embodiment, ultrasound sonications alone may not provide an effective degree of contrast in an image of a particularly treated tumor. Contrast of a tumor within an image can be enhanced through the use of contrast agents delivered into the body to the target location and/or tumor. Exemplary contrast agents include but are not limited to iron oxide contrast agents, gadolinium contrast agents, and/or other contrast agents detectable by both MRI and CT in a particular lesion. When using contrast agents, ultrasound parameters are selected to induce small vessel leaks that cause a build up of contrast agents at the ultrasound focus. The ultrasound focus is steered to the desired location associated with markings generated by the HIFU. In such embodiments, lesion conspicuity is significantly enhanced when generating an image using an exemplary imaging system such as CT, MRI and/or conventional X-ray fluoroscopy imaging.

In an exemplary embodiment, contrast agents detectable by MRI, CT, Ultrasound (US) and X-ray fluoroscopy units are used. Accordingly, the contrast agents will distribute in such a fashion as to be detected on MRI and related to a 3-dimensional image of a particular target tissue region associated with the location of a target tumor. In an exemplary embodiment, the same contrast agent distribution detected on a portal beam CT imaging system and/or fluoroscopy imaging system is used to infer tumor margins based on known anatomical relationships between contrast agent distribution and tumor margins. In an exemplary embodiment, the present disclosure provides for two effective methods to 'bake in' exemplary contrast agents:

1). In situations where contrast agents do not leak out of blood vessels relatively rapidly, it is possible to inject contrast agent(s) as a bolus and use MRI to determine the peak of a first pass through the anatomy. The system then sonicates at exactly the time associated with the peak so that blood vessels can become more permeable and very high concentrations of contrast agents are trapped in the blood vessels in and around the tumor. Although tumor vessels are typically hyper-permeable, effective sonications, adjusted appropriately, may cause cell membranes to be transiently permeable. This temporarily increases the contrast agent distribution volume since contrast agents that are usually extra-cellular can temporarily enter cells. In an exemplary embodiment, this increases the amount of contrast agent that can be trapped in a target location since the normal distribution volume of extra-cellular contrast agents is small;

2). In situations where contrast agents do leak out of blood vessels rapidly, the contrast agent is allowed to achieve a maximum concentration in target tissue and then the system sonicates at the locations where markings are desired. This effectively coagulates blood, stops blood flow, and traps the contrast agent in a desired target location.

In an exemplary embodiment, an MRI-guided HIFU system associated with the present disclosure is adapted to mark high risk areas with respect to a target tissue region such as a tumor or generate markings on a periphery of a tumor that may benefit from boosted doses of radiation. Exemplary regions include regions defined by MR spectroscopy. In this way, the markings made under MR-guidance can be used to register MR radiation therapy planning images with the radiation therapy system to better target the correct locations for treatment. In an exemplary embodiment, generating markings using MRI-guided HIFU with respect to a target location provides for an additional benefit of further ablating the target location thus providing somewhat of an additional boost dose of treatment since HIFU itself can very effectively ablate small regions at very high temperatures. This can have a particularly beneficial effect when the marks are placed in regions suspected of high tumor burden or radio-resistance, which are intended to be targeted with higher than usual radiation doses. In an exemplary embodiment, an MRI-guided HIFU system associated with the present disclosure is combined with other therapy treatments including radiation and chemotherapy.

In an exemplary embodiment, MRI is used to guide HIFU using existing MRI and HIFU hardware technology. In an exemplary embodiment, MR-guided HIFU systems generate a series of small marks around target lesions to be treated in a 3-dimensional pattern around the outside of a target tumor to clearly delineate the tumor's 3-dimensional structure. Since the total volume of marks or tags are relatively small and since control of an exemplary radiation beam is very precise, these patterns are encoded to increase lesion conspicuity thus reducing the necessity for extended and/or timely sonications.

In an exemplary embodiment, to further increase conspicuity, a contrast agent is injected intravenously promptly following marking distribution into and around the tumor. Exemplary contrast agents can be fixed into precise tissue locations using HIFU in a pattern that will clearly show the 3-dimensional shape of the tumor. In an exemplary embodiment, contrast agents can be chosen and/or developed to be visible on MRI, CT, US and/or X-ray imaging systems. In using US imaging systems, a few discrete foci of US contrast agents adapted to disperse a relatively large signal can be located relatively precisely with US and related to a 3-dimensional structure of a target tissue region.

In an exemplary embodiment, MRI can be used to monitor contrast agent distribution over time following injection, and guide the timing of the HIFU delivery so that optimal distribution of contrast media can be fixed into the tumor and/or the surrounding tissue region. MRI is then used to precisely define the relationship of the 3-dimensional distribution of contrast agent to the 3-dimensional tumor boundaries generated using the HIFU system. When the contrast media distribution is detected later by an imaging system such as cone beam CT, that distribution can be precisely related to the margins of the tumor in the therapy machine. The pattern encoded by the MRI-guided HIFU system is then detected by cone beam CT and used to determine the location of the tumor immediately before therapy is delivered to a patient while the patient is in a therapy machine associated with the cone beam CT. In an exemplary embodiment, tumor monitoring is accomplished in real time during therapy treatment and continuous adjustments to the radiotherapy beam results in response to changes detected in tumor location and deformation. Moreover, collimator configuration can be made to effectuate enhanced radiation treatment. In an exemplary embodiment, the MR diagnostic images are registered to crude RT images to provide a better guide for treatment planning and selection.

In an exemplary embodiment, marks generated by HIFU may be visible to the eye and can be used in image-guided surgery. Thus, HIFU markings may be useful in situations where radiation therapy is planned during and/or in combination with surgery. In an exemplary embodiment, small HIFU marks can be adapted to produce much less damage than the surgery itself. This would provide a way of bringing anatomic and functional MR measurements, as well as measurements using other imaging modalities directly into an operating room. A series of small but detectable HIFU marks may be advantageously effective in guiding a surgeon and providing a more precise indication of where the surgeon is cutting in relationship to a 3-dimensional MR functional and/or anatomic image. In an exemplary embodiment, fixing visually detectable contrast agents into small HIFU marks to guide the surgical approach can be useful. In an exemplary embodiment visually detectable contrast agents are designed to absorb light and/or emit light at low frequencies that can penetrate tissue to a dept of up to 1 cm. The surgeon can then use an optical detector equipped for frameless stereo-taxi to produce a 3-dimensional image of the distribution of the probe at the edges of the surgical cavity. This 3-dimensional image of the probe distribution can then be registered on an MRI image showing the relationship of the probe distribution to lesion position. This would allow surgeons to obtain a 3-dimensional view of the position of the lesion(s) relative to the surgical approach. Exemplary systems associated with the present disclosure are effective for use in combination with treatment of aneurysms, epilepsy, and other associated ailments.

In an exemplary embodiment, contrast agents are fixed onto or within a tumor and/or target tissue location using HIFU to further enhance radiation therapy. In an exemplary embodiment, gold beads are utilized as a contrast agent, delivered intravenously to enhance radiation effects. In such a scenario, the gold particles are administered intravenously and then HIFU is used to locally induce vessel leaks at the desired treatment site. Thus, gold particles will selectively accumulate at the treatment site followed by radiation therapy. In an exemplary embodiment, HIFU is used to fix the gold particles within a selective region and prevent washout by ablating blood vessels feeding and draining the region.

In an exemplary embodiment, MRI-guided HIFU is advantageously effective in cancer treatment biopsies. Often, biopsies are a very important aspect associated with cancer treatment and follow-up treatment. Many biopsies relating to cancer and treatment are performed under ultrasound guidance. However, ultrasound is often not adequate to identify the sites for biopsy. HIFU markings can be utilized such that the markings are visible under ultrasound and thus providing a means to identify locations for ultrasound guided biopsy in the context of radiotherapy interventions.

In an exemplary embodiment, MRI is used to define a 3-dimensional relationship of markings generated by the HIFU system to a tumor position and the position of other tissues and organs of interest. The MRI is used to monitor changes in these relationships associated with breathing motion and other potential disrupting motions. This relationship can then be used together with cone beam CT images of the HIFU markings to determine the 3-dimensional position of the tumor and surrounding tissues and organs.

In an exemplary embodiment, contrast agent techniques in combination with MRI-guided HIFU systems can be applied in a surgery environment. In an exemplary embodiment, optical contrast agents are trapped in a specific pattern in and around a particular lesion. For example—Using Fluorescent contrast agents allows for a wand used by a surgeon to detect the positions of these contrast agents with respect to the surgical cavity. If the excitation/detection frequencies are in a particular range, the contrast agents may be seen through the tissue. If the wand were equipped with the proper frameless stereo-taxi equipment and software, one could even construct a 3-dimensional image of the surgical cavity and the tissue immediately surrounding the cavity and show its relationship to a 3-dimensional MRI scan.

Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. A system for increasing target tissue conspicuity comprising:
   (a) an MRI-guided HIFU system for generating ablation markings on a target tissue region, the MRI-guided HIFU system including:
      (i) a transducer for delivering HIFU to the target tissue region, the delivered HIFU generating the ablation markings on the target tissue region; and
      (ii) an MRI imaging system adapted to generate a three dimensional image of the target tissue region during HIFU delivery for guiding the delivery of the HIFU to the target tissue region;
   (b) a radiotherapy delivery system for delivering radiotherapy treatment to the target tissue region;
   (c) an imaging system operable within the radiotherapy delivery system for generating a three dimensional image of the target tissue region;
   wherein the ablation markings generated on the target tissue region by the MRI-guided HIFU are visible in the three dimensional image generated by the imaging system; and
   wherein the three dimensional image generated by the imaging system guides the location of the radiotherapy treatment delivered to the target tissue region.

2. The system according to claim 1, wherein the ablation markings form a three dimensional pattern on the target tissue region, wherein the pattern is visible by the imaging system.

3. The system according to claim 2, wherein the pattern of ablation markings is a series of dots strategically positioned to provide boundaries for radiotherapy treatment delivery.

4. The system according to claim 1, wherein the ablation markings are strategically generated on the target tissue region and a contrast agent is delivered intravenously, wherein the HIFU is used to coagulate blood vessels in a selected region to trap the contrast agent at a selected point where concentration of the contrast agents is at a maximum thereby making a clear marking.

5. The system according to claim 4, wherein the HIFU is delivered before injection of the contrast agent at a power which increases vascular permeability while not ablating blood vessels thereby increasing leakage of the contrast agent to form the ablation markings.

6. The system according to claim 4, wherein the contrast agent is a member selected from the group consisting of iron oxides, gadolinium X-ray agents, conventional iodinated X-ray agents, and combinations thereof.

7. The system according to claim 4, wherein the contrast agent includes gold beads which enhance radiation intensity.

8. The system according to claim 1, wherein the radiotherapy delivery system includes a radiation beam delivery system.

9. The system according to claim 1, wherein the imaging system is a CT imaging system and the MRI-guided HIFU system is adapted to delineate the target tissue region when viewed by the CT imaging system by using high temperature ablation to create contrast.

10. The system according to claim 1, wherein the ablation markings sustain their visibility under tissue deformation.

11. The system according to claim 1, wherein the radiotherapy delivery system includes an Intensity-Modulated Radiation Therapy (IMRT) system.

12. A method of increasing the conspicuity of a target tissue region for receiving radiotherapy treatment comprising the steps of:
   generating ablation markings which are visible by an imaging system on the target tissue region by ablating the target tissue region with an MRI-guided HIFU system including a transducer delivering HIFU to target locations on the target tissue region;
   guiding, during the delivery of the HIFU, the transducer with an MRI imaging system;
   monitoring a position and/or location of the target tissue region using the imaging system concurrently with delivering a radiation therapy beam to the target tissue region with a radiotherapy delivery system;
   guiding, with the imaging system, the delivery of the radiotherapy beam by the radiotherapy delivery system continuously in real time.

13. The method according to claim 12, further comprising:
   delivering the HIFU at a power which increases vascular permeability while not ablating blood vessels;
   intravenously delivering a contrast agent into the target tissue region to form the ablation markings, the increased vascular permeability causing leakage of the contrast agent.

14. The method according to claim 12, further comprising:
   continuously adjusting positioning of the radiotherapy beam in real time to simultaneously increase a dosage directed to the target tissue region and reduce radiation exposure to surrounding non-target tissue regions.

15. The method according to claim 12, further comprising:
   encoding the ablation markings;
   registering and verifying the encoded ablation markings in future imaging of the target tissue region for future treatment planning strategy.

16. The method according to claim 12, further comprising:
   to providing image guidance, using the MRI-guided HIFU system, to a surgeon performing at least one of surgery and a biopsy on the target tissue region.

17. The method according to claim 12, wherein the target tissue region is a tumor.

18. A method of increasing conspicuity of a target in a target tissue region to receive radiotherapy treatment, comprising:
   imaging the target tissue region using magnetic resonance (MR) to generate an MR image;
   guiding a HIFU system to focus HIFU on target locations using the MR image;
   delivering HIFU to the target locations to generate ablation markings which are visible with a CT imaging system at the target locations;

imaging, with the CT imaging system, the target tissue region to generate CT images in which the ablation markings are visible;

guiding a radiotherapy system to deliver a radiotherapy beam to the target tissue region based on locations of the ablation markings in the CT images.

19. The method according to claim 18, wherein the ablation makings include a three dimensional pattern of dots that define boundaries of the target tissue region.

20. The method according to claim 18, further comprising:

intravenously delivering a contrast agent to the target tissue region;

coagulating, with the delivered HIFU, blood vessels at the target locations to trap the contrast agent to generate the ablation markings.

21. The method according to claim 18, further comprising:

increasing, with the delivered HIFU, vascular permeability of blood vessels at the target locations without ablating the blood vessels; and intravenously delivering a contrast agent in the blood vessels wherein the contrast agent leaks from the blood vessels at the target locations to generate the ablation markings.

22. The method according to claim 18, further comprising:

guiding the HIFU system to focus the HIFU on further locations that mark an area of risk;

delivering the HIFU to the further locations to generate risk area markings which are visible in the CT images;

guiding the radiotherapy system to deliver the radiotherapy beam to avoid the high risk area.

* * * * *